(12) United States Patent
Maier et al.

(10) Patent No.: US 7,151,816 B2
(45) Date of Patent: Dec. 19, 2006

(54) IMAGING TOMOGRAPHY APPARATUS HAVING AN ATTACHED PATIENT SUPPORT WITH A MOVABLE BACKREST

(75) Inventors: Sebastian Maier, Augsburg (DE); Klaus Thormann, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/072,945

(22) Filed: Mar. 3, 2005

(65) Prior Publication Data
US 2005/0204473 A1    Sep. 22, 2005

(30) Foreign Application Priority Data
Mar. 3, 2004    (DE) ..................... 10 2004 010 955

(51) Int. Cl.
*H05G 1/60* (2006.01)
*H05G 1/00* (2006.01)

(52) U.S. Cl. ............................ 378/20; 378/4; 378/208

(58) Field of Classification Search ................. 378/20, 378/79, 195, 208; 5/618, 610, 601, 624; 297/325
See application file for complete search history.

(56) References Cited

U.S. PATENT DOCUMENTS

| | | | | |
|---|---|---|---|---|
| 4,409,695 A * | 10/1983 | Johnston et al. | ................ | 5/601 |
| 4,961,208 A * | 10/1990 | Okada | ......................... | 378/18 |
| 5,703,922 A * | 12/1997 | Rattner | ......................... | 378/65 |
| 6,217,214 B1 * | 4/2001 | Cabral et al. | ................ | 378/196 |
| 6,322,251 B1 | 11/2001 | Ballhaus et al. | | |
| 6,618,613 B1 * | 9/2003 | Shukla et al. | ................ | 600/425 |
| 6,912,746 B1 * | 7/2005 | Grove | ......................... | 5/618 |
| 2003/0142791 A1 | 7/2003 | Barde et al. | | |
| 2005/0195944 A1 * | 9/2005 | Bartels et al. | ............... | 378/195 |

\* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

An imaging tomography apparatus, such as an x-ray computed tomography apparatus or a magnetic resonance tomography apparatus, has a patient bed that can be driven into a tunnel-shaped or annular data acquisition device. To increase comfort for the patient and accessibility by medical personnel, the patient bed has a pivotable backrest connected to a seat.

9 Claims, 3 Drawing Sheets

IMAGING TOMOGRAPHY APPARATUS HAVING AN ATTACHED PATIENT SUPPORT WITH A MOVABLE BACKREST

BACKGROUND OF THE INVENTION

1. Field of the Invention

The present invention concerns an imaging tomography apparatus, in particular an x-ray computed tomography apparatus or magnetic resonance tomography apparatus of the type having a patient bed that is driven into and out of a data acquisition device (scanner).

2. Description of the Prior Art

X-ray computed tomography and magnetic resonance tomography systems are known as imaging tomography apparatuses or systems. A common feature of such tomography apparatuses is a tube-shaped or tunnel-shaped data acquisition device (scanner). For data acquisition, the patient is horizontally moved into the scanner on a patient bed mounted at the tomography apparatus. The patient bed also can be vertically movable. This makes it easier to place the patient on the patient bed or to disembark after the scan, in particular for injured or elderly patients.

In practice, sometimes a procedure must be conducted on the patient for preparation of the scan. For example, it may be necessary to administer a contrast agent to the patient by means of an infusion. Independent of this, it is conceivable that the patient must be operated on immediately after the measurement, while still on the patient bed. A problem thus sometimes occurs that the surgery region of the patient is difficult to access for the medical auxiliary personnel or the surgeon.

SUMMARY OF THE INVENTION

An object of the invention to provide an imaging tomography apparatus that avoids the aforementioned disadvantages. In particular, such an imaging tomography apparatus should enable improved access to a surgery region of the patient. A further object of the invention is to provide such an imaging tomography apparatus that enables improved accessibility for injured or elderly patients at the patient bed.

This object is achieved in accordance with the invention by an imaging tomography apparatus having a patient bed with a pivotable backrest connected to a seat. The position of the patient accommodated on the patient bed can be changed by pivoting the backrest relative to the seat. This eases the accessibility to a surgical procedure region on the patient. In particular injured patients can be placed in a sitting position, which is more comfortable under the circumstances, until implementation of the scan.

The patient bed thus can be moved horizontally, accommodated on a mounting device attached on the data acquisition device. The patient bed in particular can be moved horizontally along a tunnel or tube axis of the scanner. This enables an in-and-out deployment of the patient accommodated on the patient bed in the data acquisition device. Attached on the mounting device, the patient bed can appropriately be pivoted on a y-axis proceeding perpendicularly to the tunnel or tube axis. This enables the production of slice images disposed at an angle through the body axis of the patient. Furthermore, the patient can be brought into an operating position that is optimal for the medical auxiliary personnel or the surgeon.

In an embodiment of the invention, the patient bed has a foot part connected with the seat such that the foot part can pivot relative to the seat. The three-part execution of the patient bed further increases the freedom for positioning the patient. Accessibility to a surgery area is further improved. Accessibility for the patient to the patient bed is further simplified, for example for handicapped patients.

In a further embodiment, the mounting device is attached to the measurement device such that it can move vertically. In a preferred embodiment the data acquisition device, together with the mounting device attached thereto, is movably attached to a base (pedestal). In comparison to known apparatuses, this embodiment allows lowering of the patient bed particularly far down in the vertical direction. This further eases the accessibility to the patient bed.

For execution of the horizontal and/or vertical movements, electrically-driven adjustment devices are appropriately provided. To pivot the backrest and/or the foot part and/or the patient bed, electrically-driven pivot devices can be provided. The pivot devices are executed such that data acquisition by the scanner is not affected by them. In particular metallic parts of the pivot devices are located outside of the scan region of the patient bed. For example, they can be accommodated into the mounting device.

A control device can be provided to control the movements (preferably the pivot movements) of the patient bed. By means of such a control device, the patient bed can be automatically brought into a predetermined measurement position.

DESCRIPTION OF THE PREFERRED EMBODIMENTS

Figure 1:
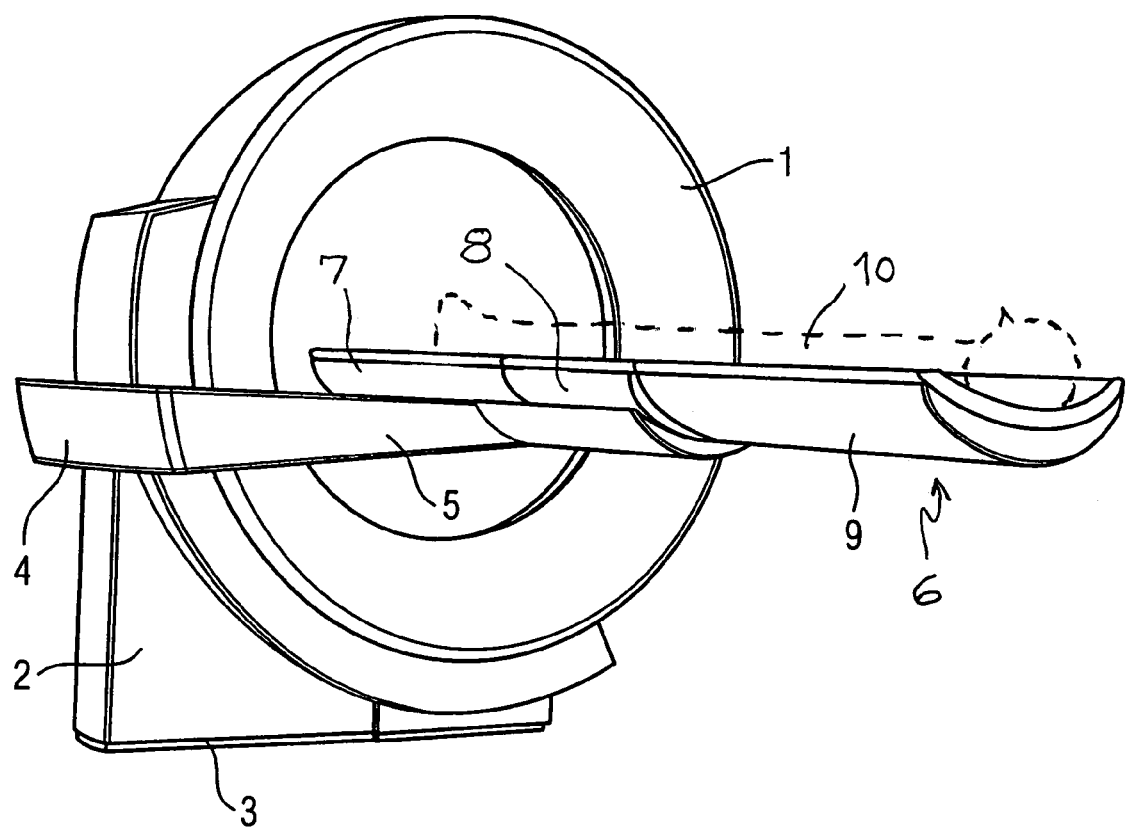
FIG. 1 is a perspective view of a tomography apparatus with a horizontal patient bed in a first vertical position, in accordance with the invention.

A tomography apparatus is shown in FIGS. 1 through 5 in the example of an x-ray computed tomography apparatus. An annularly fashioned data acquisition device or gantry 1 is accommodated on a carrier 2. The carrier 2 is supported on a base 3 such that the carrier 2 can be moved vertically. In addition, a hydraulically-operable or electrically-operable lifting device (not shown) is provided. A mounting device 4 that can be moved vertically is in turn attached to the carrier 2. A mounting arm 5 of the mounting device 4 accommodates a patient bed 6 such that it can move horizontally. The patient bed 6 can move horizontally, in particular parallel to the axis of the data acquisition device 1. As is best seen from FIG. 4, the patient bed 6 is formed of a backrest 7, a seat 8 and a foot part 9. For vertical movement of the mounting device 5, a further hydraulically-operable or electrically-operable lifting device (not shown) is provided. A preferably electrically-operable horizontal movement device (not shown) is likewise provided for horizontal movement of the patient bed 6. The horizontal movement device can be disposed in the mounting arm 5. In particular, electrically-operable pivot devices (not shown) are provided to pivot the backrest 7 as well as the foot part 9.

Figure 2:
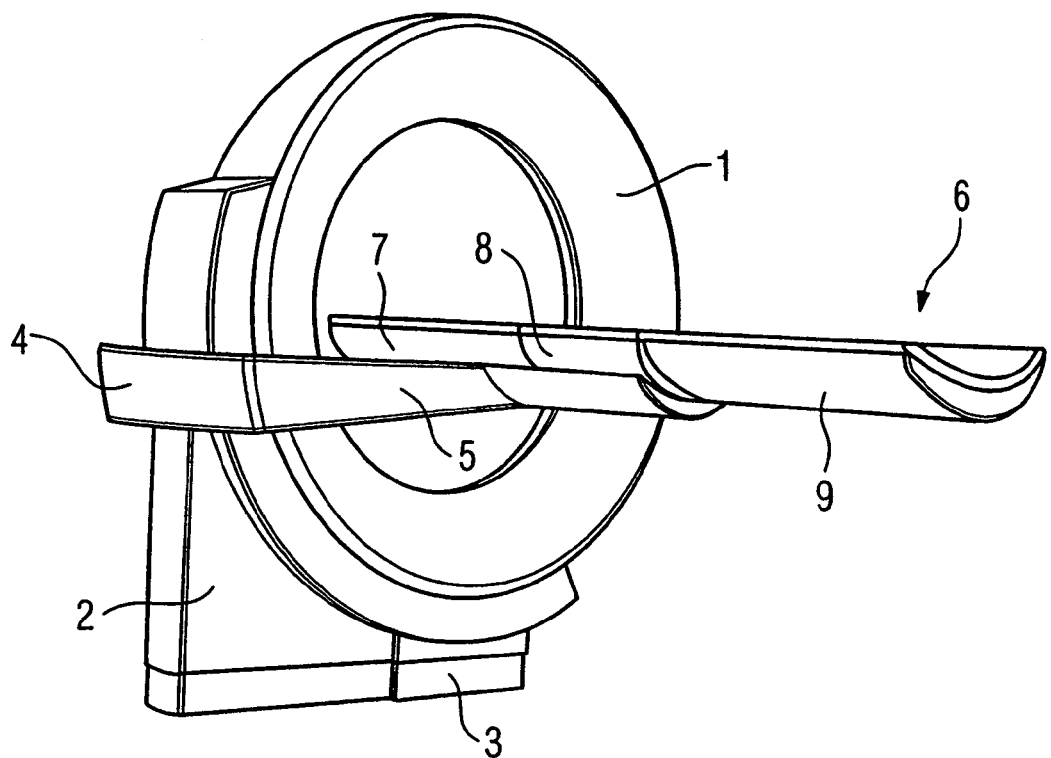
FIG. 2 shows the tomography apparatus according to FIG. 1 in a second vertical position.
Figure 3:
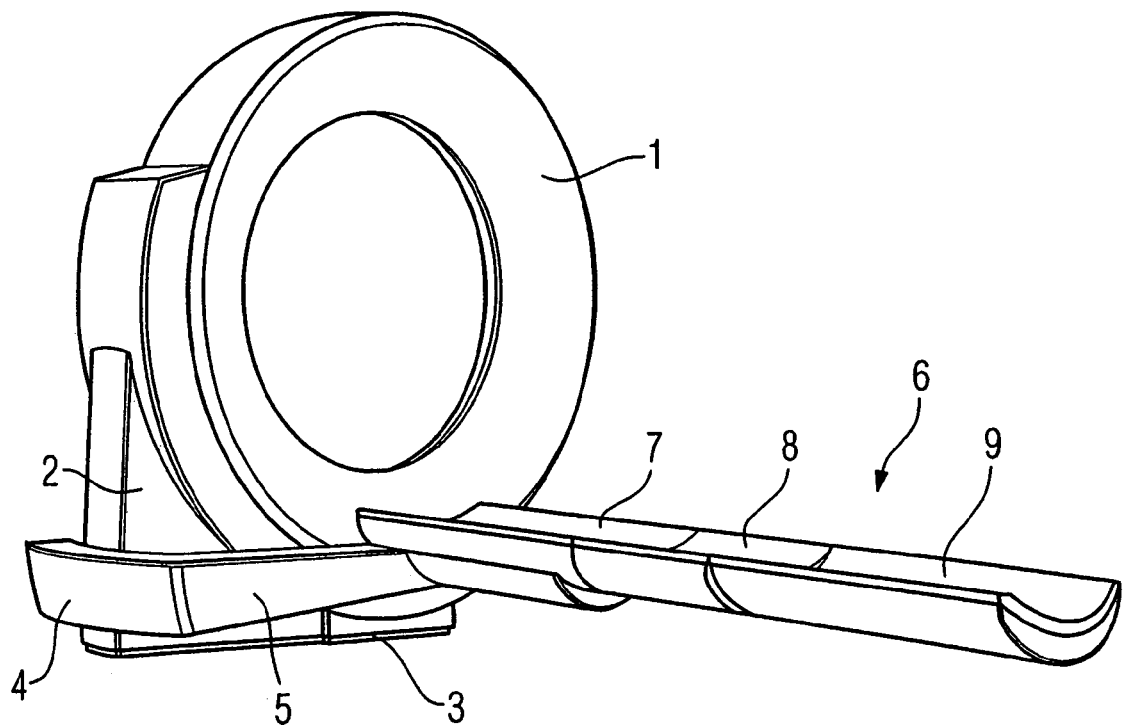
FIG. 3 shows the tomography apparatus according to FIG. 1 in a third position.
Figure 4:
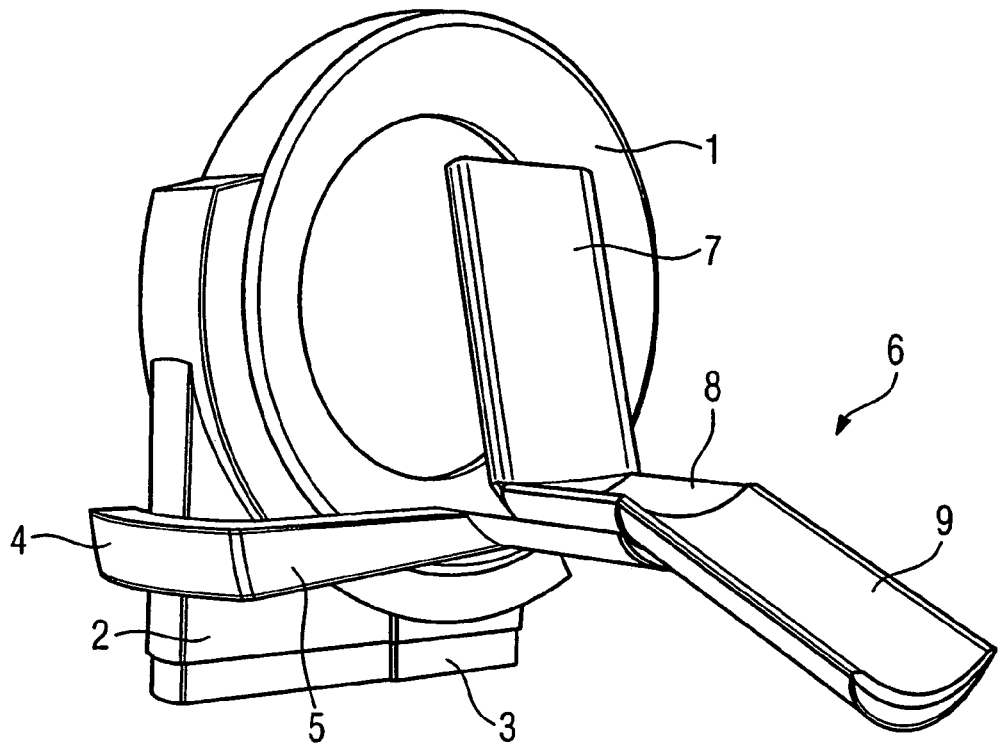
FIG. 4 shows the tomography apparatus according to FIG. 1 with the patient bed located in the sitting position.

The functioning of the x-ray computed tomography apparatus is as follows:

Because the mounting device 4 can be moved vertically on the carrier 2, and this is in turn attached to the base 3 such that it can move vertically, the patient bed 6 can be moved particularly far in the vertical direction. FIG. 1 shows an x-ray computed tomography apparatus in a first vertical position, in which the carrier 2 is not raised relative to the base 3. FIG. 2 shows the patient bed 6 in a highest second vertical position, in which the carrier 2 is vertically raised relative to the base 3. FIG. 3 shows the patient bed 6 in a lowest third position. The carrier 2 is likewise in a position that is vertically lowered relative to the base 3. The pivoting capability of the backrest 7 and the seat 9 enable the patient bed 6 to be adjusted to a seating position. This eases accessibility to a surgery region at the patient 10 (FIG. 1).

Figure 5:
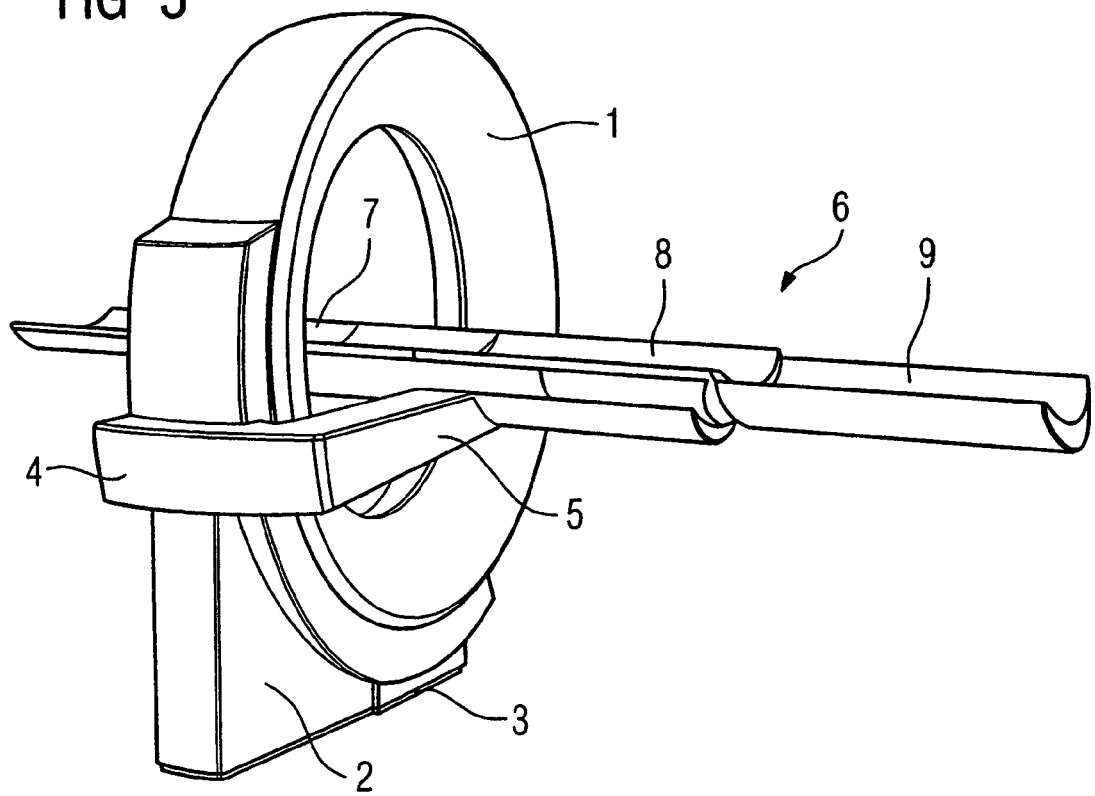
FIG. 5 shows the tomography apparatus according to FIG. 1 with the patient bed moved into the measurement device.

For data acquisition (conducting a scan), the patient bed 6 can be automatically set in a horizontal position and horizontally moved into the data acquisition device 1 by a control device (not shown). FIG. 5 shows the patient bed 6 in the measurement position.

The disclosed patient bed as well as its movement possibilities can be used not only in connection with an x-ray computed tomography apparatus, but also with any similarly-designed tomography apparatus. In this category are, for example, a magnetic resonance tomography apparatus and geometrically similarly-designed nuclear medicine apparatuses.

Although modifications and changes may be suggested by those skilled in the art, it is the intention of the inventors to embody within the patent warranted hereon all changes and modifications as reasonably and properly come within the scope of their contribution to the art.

We claim as our invention:

1. An imaging tomography apparatus comprising:
   gantry having an opening therein adapted to receive a patient for acquiring measurement data from the patient in the data acquisition device;
   a carrier on which said gantry is disposed;
   a patient bed adapted to receive the patient thereon, said patient bed being movable into and out of said opening;
   said patient bed comprising a seat and a backrest connected to said seat so as to be pivotable relative to said seat;
   a mounting device attached to said carrier that attaches said patient bed to said carrier; and
   a base on which said carrier is supported that allows said carrier together with said mounting device to move vertically.

2. An imaging tomography apparatus as claimed in claim 1 wherein said patient bed comprises a foot part connected to said seat so as to be pivotable relative to said seat.

3. An imaging tomography apparatus as claimed in claim 1 wherein said opening has a longitudinal axis, and wherein said mounting device comprises a pivot allowing pivoting of said patient bed around an axis substantially perpendicular to said longitudinal axis.

4. An imaging tomography apparatus as claimed in claim 1 wherein said base comprises an electrically driven prime mover for effecting vertical movement of said gantry together with said mounting device.

5. An imaging tomography apparatus as claimed in claim 1 comprising an electrically driven prime mover connected to said patient bed for moving said patient bed into and out of said opening.

6. An imaging tomography apparatus as claimed in claim 1 comprising an electrically driven prime mover for pivoting said backrest relative to said seat.

7. An imaging tomography apparatus as claimed in claim 6 comprising a control unit connected to said prime mover for controlling pivoting of said patient bed relative to said seat.

8. An imaging tomography apparatus as claimed in claim 1 wherein said patient bed comprises a foot part attached to said seat so as to pivotable relative to said seat, and comprising an electrically driven first prime mover for pivoting said backrest relative to said seat, and an electrically driven second prime mover for pivoting said foot part relative to said seat.

9. An imaging tomography apparatus as claimed in claim 8 comprising a control unit for controlling said first and second prime movers for respectively controlling pivoting of said backrest and said foot part relative to said seat.

* * * * *